US012802229B2

(12) United States Patent
Yoda et al.

(10) Patent No.: US 12,802,229 B2
(45) Date of Patent: Nov. 17, 2026

(54) MEDICAL IMAGE PROCESSING APPARATUS, MEDICAL IMAGE PROCESSING METHOD, AND NON-TRANSITORY COMPUTER READABLE MEDIUM

(71) Applicant: Canon Kabushiki Kaisha, Tokyo (JP)

(72) Inventors: Takahiro Yoda, Nasushiobara (JP); Yojiro Suzuki, Oyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 228 days.

(21) Appl. No.: 18/662,161

(22) Filed: May 13, 2024

(65) Prior Publication Data

US 2024/0386565 A1 Nov. 21, 2024

(30) Foreign Application Priority Data

May 15, 2023 (JP) ................................ 2023-080254

(51) Int. Cl.
*G06T 7/00* (2017.01)
*A61B 6/58* (2024.01)

(52) U.S. Cl.
CPC ............ *G06T 7/0016* (2013.01); *A61B 6/586* (2013.01); *G06T 2207/10116* (2013.01); *G06T 2207/20092* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 6,529,618 B1 * | 3/2003 | Ohara | G06T 12/10 | 382/141 |
| 2005/0063513 A1 * | 3/2005 | Hsieh | A61B 6/585 | 378/98.8 |
| 2010/0303208 A1 * | 12/2010 | Baruth | A61B 6/585 | 378/98.8 |
| 2014/0184383 A1 * | 7/2014 | Wodnicki | A61B 6/586 | 340/4.3 |
| 2016/0015351 A1 * | 1/2016 | Konno | A61B 6/5258 | 378/62 |
| 2019/0029628 A1 * | 1/2019 | Konno | A61B 6/542 | |
| 2019/0050970 A1 * | 2/2019 | Cresens | G06T 5/77 | |

FOREIGN PATENT DOCUMENTS

JP 2010-246714 A 11/2010

* cited by examiner

*Primary Examiner* — Soo Shin
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry acquires, from a storage unit that stores defect maps indicating an arrangement of defective detection elements in an X-ray detector including a plurality of detection elements that detect X-rays, a plurality of the defect maps at different timings, generates an interpolation target map regarding the positions of some of the detection elements included in any of the plurality of the acquired defect maps, and generates interpolated data, in which detection results by the X-ray detector are interpolated, on the basis of the generated interpolation target map.

12 Claims, 10 Drawing Sheets

MEDICAL IMAGE PROCESSING APPARATUS, MEDICAL IMAGE PROCESSING METHOD, AND NON-TRANSITORY COMPUTER READABLE MEDIUM

CROSS-REFERENCE TO RELATED APPLICATIONS

This application is based upon and claims the benefit of priority from Japanese Patent Application No. 2023-080254, filed on May 15, 2023, the entire contents of which are incorporated herein by reference.

FIELD

Embodiments described herein relate generally to a medical image processing apparatus, a medical image processing method, and a non-transitory computer readable medium.

BACKGROUND

In the related art, a medical image processing apparatus such as a PCCT apparatus that performs photon counting X-ray computed tomography has a function of periodically performing calibration and masking detection results of defective detection elements in an X-ray detector. When the detection results are masked by such a function, the medical image processing apparatus does not use the masked detection results, and generates interpolated data by using detection results around the masked detection elements, or the like In order to generate image data free of artifacts or the like, the medical image processing apparatus preferably masks detection results of all defective detection elements detected by each calibration.

However, defective detection elements may fluctuate between outputting normal and abnormal detection results each time calibration is performed. When the medical image processing apparatus permanently masks the detection results of the defective detection elements, the number of unmasked detection elements may be reduced. That is, in the medical image processing apparatus, the number of detection elements whose detection results are available may be reduced.

DETAILED DESCRIPTION

A medical image processing apparatus according to an embodiment includes processing circuitry. The processing circuitry acquires, from a storage unit that stores defect maps indicating an arrangement of defective detection elements in an X-ray detector including a plurality of detection elements that detect X-rays, a plurality of the defect maps at different timings, generates an interpolation target map regarding the positions of some of the detection elements included in any of the plurality of the acquired defect maps, and generates interpolated data, in which detection results by the X-ray detector are interpolated, on the basis of the generated interpolation target map.

The medical image processing apparatus, a medical image processing method, and a non-transitory computer readable medium related to the present embodiment are described below with reference to the drawings. In the following embodiments, parts with the same reference signs are assumed to operate in the same way, and duplicate explanations thereof are omitted as appropriate.

For the sake of specificity of explanation, the medical image processing apparatus according to the embodiment is assumed to be an X-ray computed tomography (CT) apparatus. More specifically, the medical image processing apparatus according to the embodiment is described as a photon counting X-ray CT apparatus (hereinafter, referred to as a PCCT apparatus). The PCCT apparatus is, for example, an apparatus that can reconstruct X-ray CT image data with a high signal-to-noise ratio by counting X-rays transmitted through a subject by using a direct-conversion X-ray detector. The medical image processing apparatus according to the embodiment may be an X-ray CT apparatus with an integrating X-ray detector instead of a photon-counting X-ray detector. The medical image processing apparatus may also be a medical image processing apparatus for general imaging with an X-ray flat panel detector, a medical image processing apparatus for circulatory organs (blood vessel imaging apparatus (angiography)), or a mammography apparatus.

First Embodiment

Figure 1:
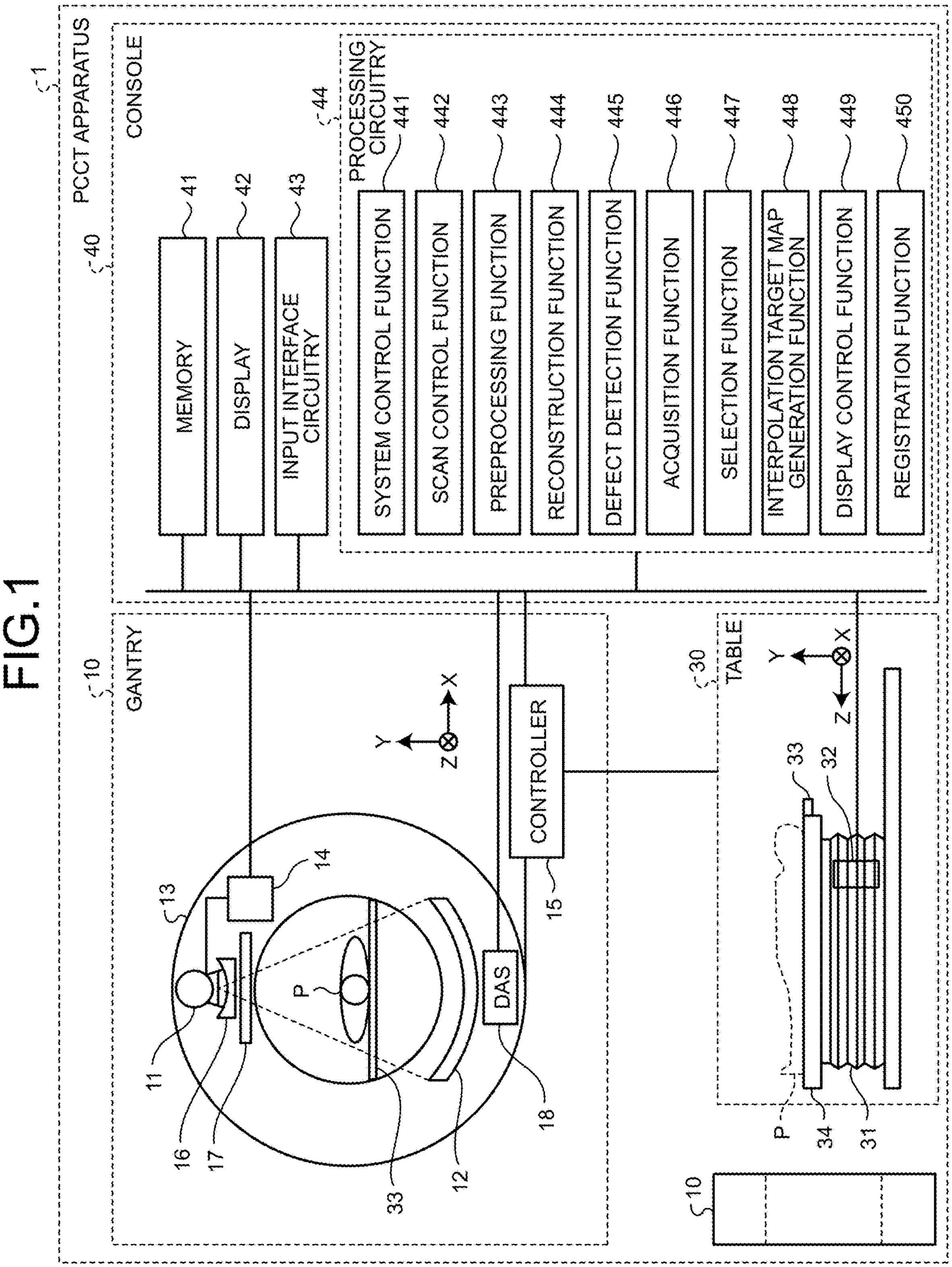
FIG. 1 is a diagram illustrating an example of the configuration of a PCCT apparatus according to a first embodiment.

FIG. 1 is a diagram illustrating an example of the configuration of a PCCT apparatus 1 according to a first embodiment. As illustrated in FIG. 1, the PCCT apparatus 1 includes a gantry 10, a table 30, and a console 40. In the present embodiment, the longitudinal direction of a rotation axis of a rotation frame 13 or a table-top 33 of the table 30 in a non-tilted state is defined as a Z-axis direction, an axis direction orthogonal to the Z-axis direction and horizontal to a floor surface is defined as an X-axis direction, and an axis direction orthogonal to the Z-axis direction and perpendicular to the floor surface is defined as a Y-axis direction. For the sake of explanation, FIG. 1 illustrates a plurality of gantry 10; however, an actual configuration of the PCCT apparatus 1 includes only one gantry 10.

The gantry 10 and the table 30 operate on the basis of an operation from a user via the console 40 or an operation from a user via an operating unit provided on the gantry 10 or the table 30. The gantry 10, the table 30, and the console 40 are communicably connected to one another in a wired or wireless manner.

The gantry 10 is an apparatus with an imaging system that irradiates a subject P with X-rays and collects detection data of the X-rays transmitted through the subject P. More specifically, the gantry 10 includes an X-ray tube 11 (X-ray generator), a wedge 16, a collimator 17, an X-ray detector 12, X-ray high voltage circuitry 14, a data acquisition system (DAS) 18, the rotation frame 13, and a controller 15.

The X-ray tube 11 is a vacuum tube that generates X-rays by emitting thermo electrons from a cathode (filament) toward an anode (target) due to the application of a high voltage and the supply of a filament current from X-ray high voltage circuitry 14. The X-rays are generated when the thermo electrons collide with the target. The X-rays generated at the tube focus of the X-ray tube 11 are formed into a cone-beam form via the collimator 17, for example, and are emitted to the subject P. For example, the X-ray tube 11 includes a rotating anode type X-ray tube that generates X-rays by irradiating a rotating anode with thermo electrons.

As illustrated in FIG. 1, the X-rays emitted in the cone-beam form spread in a fan shape in the X-axis direction. Therefore, an angle indicating the spread in the X-axis direction of the X-rays emitted in the cone-beam form is referred to as a fan angle. An angle indicating the depth in the Z-axis direction of the X-rays emitted in the cone-beam form is referred to as a cone angle. Therefore, the X-axis direction is also referred to as a fan angle direction and the Z-axis direction is also referred to as a cone angle direction.

The X-ray detector 12 detects photons of the X-rays generated by the X-ray tube 11. Specifically, the X-ray detector 12 detects the X-rays emitted from the X-ray tube 11 and passing through the subject P in units of photons, and outputs an electrical signal corresponding to the X-ray dose to the DAS 18. The X-ray detector 12, for example, includes a plurality of detection element arrays each including a plurality of detection elements (also referred to as X-ray detection elements) arranged in the fan angle direction (also referred to as a channel direction) along one circular arc centered at the focus of the X-ray tube 11. In the X-ray detector 12, the plurality of detection element arrays are flatly arranged along the Z-axis direction. That is, the X-ray detector 12 has, for example, a structure in which the plurality of detection element arrays are flatly arranged along the cone angle direction (also referred to as a row direction or a slice direction).

That is, the X-ray detector 12 includes a plurality of detection elements arranged in a two-dimensional direction. The X-ray detector 12 is a photon counting X-ray detector. The X-ray detector 12 includes, for example, a direct conversion X-ray detector with semiconductor elements that directly convert incident X-rays into electrical signals. The X-ray detector 12 may include an indirect conversion X-ray detector instead of a direct conversion X-ray detector.

The PCCT apparatus 1 has various types, such as a rotate/rotate-type ($3^{rd}$ generation CT) in which the X-ray tube 11 and the X-ray detector 12 rotate around the subject P as a single unit, and a stationary/rotate-type ($4^{th}$ generation CT) in which many detection elements arrayed in a ring shape are fixed and only the X-ray tube 11 rotates around the subject P, and any of these types can be applied to the present embodiment.

The X-ray detector 12 is a direct conversion X-ray detector with semiconductor elements that convert incident X-rays into electrical charge. The X-ray detector 12 in the present embodiment, for example, includes at least one high-voltage electrode, at least one semiconductor crystal, and a plurality of readout electrodes. The semiconductor element is also referred to as an X-ray conversion element. The semiconductor crystal is implemented by, for example, cadmium telluride (CdTe), cadmium zinc telluride (CdZnTe: CZT), or the like. In the X-ray detector 12, electrodes are provided on two surfaces that face each other across the semiconductor crystal and are orthogonal to the Y direction. That is, the X-ray detector 12 is provided with a plurality of anode electrodes (also referred to as readout electrodes or pixel electrodes) and a cathode electrode (also referred to as common electrode) across the semiconductor crystal. Hereafter, a surface formed by the cathode electrode is referred to as a cathode surface.

A bias voltage is applied between the readout electrode and the common electrode. In the X-ray detector 12, when X-rays are absorbed by the semiconductor crystal, electron-hole pairs are generated, with the electrons moving to the anode electrode side (readout electrode side) and the holes moving to the cathode electrode side, so that signals related to X-ray detection are output from the X-ray detector 12 to the DAS 18.

The X-ray detector 12 is not limited to the photon counting X-ray detector, and may also be an integrating (also referred to as a current mode measurement or energy integrating) X-ray detector. In such a case, the integrating X-ray detector includes either a direct or indirect conversion X-ray detector. For example, the X-ray detector 12 may include, as an integrating X-ray detector, an X-ray flat panel detector (FPD) used for general X-ray photography.

The rotation frame 13 rotatably supports the X-ray tube 11 and the X-ray detector 12 around the rotating axis thereof. Specifically, the rotation frame 13 supports the X-ray tube 11 and the X-ray detector 12 so as to be opposite each other. The rotation frame 13 is an annular frame that rotates the X-ray tube 11 and the X-ray detector 12 by the controller 15 to be described below. The rotation frame 13 is rotatably supported by a fixed frame made of metal such as aluminum. The rotation frame 13 rotates around the rotating axis at a constant angular velocity under power from a drive mechanism of the controller 15.

The rotation frame 13 can further support X-ray high voltage circuitry 14 and the DAS 18 in addition to the X-ray tube 11 and the X-ray detector 12. Such a rotation frame 13 is housed in a substantially cylindrical housing formed with an opening (bore) that forms an imaging space. The central axis of the opening coincides with the rotating axis of the rotation frame 13.

X-ray high voltage circuitry 14 includes a high voltage generator having electrical circuits such as a transformer and a rectifier and having a function of generating a high voltage to be applied to the X-ray tube 11 and a filament current to be supplied to the X-ray tube 11, and an X-ray control apparatus that controls an output voltage according to the X-rays emitted by the X-ray tube 11. The high voltage generator may be of a transformer type or an inverter type. X-ray high voltage circuitry 14 may be provided on the rotation frame 13 or on a fixed frame (not illustrated) side of the gantry 10. The fixed frame is a frame that rotatably supports the rotation frame 13.

The controller 15 includes processing circuitry having a central processing unit (CPU) or the like, and a drive mechanism such as a motor and an actuator. The processing circuitry includes, as hardware resources, a processor such as a CPU or a micro processing unit (MPU) and a memory such as a read only memory (ROM) or a random access memory (RAM). The controller 15 may be implemented, for example, by a processor such as a graphics processing unit (GPU), an application specific integrated circuit (ASIC), or a programmable logic device (for example, a simple programmable logic device (SPLD), a complex programmable logic device (CPLD), and a field programmable gate array (FPGA)).

When the processor is, for example, a CPU, the processor implements functions by reading and executing computer programs stored in the memory. On the other hand, when the processor is, for example, an ASIC, the functions are directly incorporated in the circuitry of the processor as logic circuitry instead of storing the computer programs in the memory. Each processor of the present embodiment is not limited to being configured as a single piece of circuitry for each processor, and one processor may be configured by combining a plurality of pieces of independent circuitry to implement the functions thereof. The plurality of components may be integrated into one processor to implement the functions thereof.

The controller 15 also has a function of controlling the operations of the gantry 10 and the table 30 by receiving input signals from the console 40 or an input interface circuitry 43 attached to the gantry 10. For example, the controller 15 controls the rotation of the rotation frame 13, the tilt of the gantry 10, and the operations of the table 30 and the table-top 33 upon receiving the input signals. The control of tilting the gantry 10 may be implemented by the controller 15 that rotates the rotating frame 13 around an axis parallel to the X-axis direction according to inclination angle (tilt angle) information input by the input interface circuitry 43 attached to the gantry 10. The controller 15 may be provided in the gantry 10 or in the console 40.

The wedge 16 is a filter for adjusting the amount of X-rays emitted from the X-ray tube 11. Specifically, the wedge 16 is a filter that transmits and attenuates the X-rays emitted to the subject P from the X-ray tube 11 so that the X-rays have a predetermined distribution. The wedge 16 is, for example, a wedge filter or a bow-tie filter, and is a filter made of aluminum machined to have a predetermined target angle and a predetermined thickness.

The collimator 17 is a lead plate or the like for narrowing down an X-ray irradiation range of the X-rays transmitted through the wedge 16, and forms a slit by combining a plurality of lead plates or the like.

The data acquisition system (DAS) 18 includes a plurality of pieces of counting circuitry. Each of the plurality of pieces of counting circuitry includes an amplifier that performs an amplification process on the electrical signal output from each detection element of the X-ray detector 12 and an A/D converter that converts the amplified electrical signal into a digital signal, and generates detection data that is the result of the counting process using the detection signal of the X-ray detector 12. The result of the counting process is data in which the number of photons of X-rays per energy bin is assigned. The energy bin corresponds to an energy range of a predetermined width. For example, the DAS 18 counts photons (X-ray photons) originating from the X-rays emitted from the X-ray tube 11 and transmitted through the subject P, and generates, as detection data, the result of the counting process that discriminates the energy of the counted photons. The DAS18 is an example of a data collection unit.

The detection data generated by the DAS 18 is transmitted to the console 40. The detection data is a set of data including a channel number and a column number of a detector pixel from which the detection data is generated, a view number indicating a collected view (also referred to as a projection angle), and a value indicating a detected X-ray dose. As the view number, an order in which the views are collected (collection time) may be used, or a number (for example, 1 to 1000) representing the rotation angle of the X-ray tube 11 may be used. Each of the plurality of pieces of counting circuitry in the DAS 18 is implemented, for example, by a group of circuitry provided with circuit elements capable of generating detection data. In the present embodiment, when simply referred to as "detection data", it encompasses both pure raw data detected by the X-ray detector 12 and before preprocessing, and raw data obtained by preprocessing the pure raw data. The data before preprocessing (detection data) and the data after preprocessing may be collectively referred to as projection data.

The table 30 is an apparatus for placing and moving the subject P to be scanned, and includes a base 31, table drive circuitry 32, the table-top 33, and a table-top support frame 34. The base 31 is a housing that supports the table-top support frame 34 in a vertically movable manner. table drive circuitry 32 is a motor or an actuator for moving the table-top 33 with the subject P placed thereon in the direction of a long axis of the table-top 33. table drive circuitry 32 moves the table-top 33 under the control of the console 40 or under the control of the controller 15. The table-top 33 provided on an upper surface of the table-top support frame 34 is a board on which the subject P is placed. In addition to the table-top 33, table drive circuitry 32 may move the table-top support frame 34 in the direction of the long axis of the table-top 33.

The console 40 is an apparatus that controls the gantry 10 and generates CT image data based on the results of scan by the gantry 10. The console 40 includes a memory 41 (storage unit), a display 42 (display unit), the input interface circuitry 43 (input unit), and processing circuitry 44 (processing unit). Data communication among the memory 41, the display 42, the input interface circuitry 43, and the processing circuitry 44 is performed via a bus (BUS).

The memory 41 is implemented by a semiconductor memory element such as a random access memory (RA) and a flash memory, a hard disk drive (HDD), a solid state drive (SSD), an optical disk, or the like. The memory 41 may be a drive device that reads and writes various information between a portable storage medium such as a compact disc (CD), a digital versatile disc (DVD), and a flash memory, and a semiconductor memory element such as a random access memory (RAM). The memory 41 stores, for example, projection data and reconstructed image data. A storage area of the memory 41 may be in the PCCT apparatus 1 or in an external storage device connected by a network. The memory 41 stores a control program according to the present embodiment. The memory 41 is an example of a storage unit.

The display 42 displays various information. For example, the display 42 outputs medical images (CT images) generated by the processing circuitry 44, a graphical user interface (GUI) for receiving various operations from an operator, and the like. For example, as the display 42, a liquid crystal display (LCD), an organic electro luminescence display (OELD), a plasma display, or any other displays can be used as appropriate. The display 42 may be provided on the gantry 10. The display 42 may be of a desktop type or may be configured as a tablet terminal or the like capable of wirelessly communicating with the body of the console 40.

The input interface circuitry 43 receives various input operations from an operator, converts the received input operations into electrical signals, and outputs the electrical signals to the processing circuitry 44. For example, the input interface circuitry 43 receives, from the operator, collection conditions for collecting projection data, reconstruction conditions for reconstructing CT images, image processing conditions for generating post-processed images from the CT images, or the like. As the input interface circuitry 43, for example, a mouse, a keyboard, a trackball, a switch, a button, a joystick, a touchpad, a touch panel display, or the like can be used as appropriate.

In the present embodiment, the input interface circuitry 43 is not limited to those with physical operating components such as a mouse, a keyboard, a trackball, a switch, a button, a joystick, a touchpad, and a touch panel display. For example, an example of the input interface circuitry 43 also includes electrical signal processing circuitry that receives an electrical signal corresponding to an input operation from an external input device provided separately from the device and outputs the electrical signal to the processing circuitry 44. The input interface circuitry 43 is an example of an input unit. The input interface circuitry 43 may be provided on the gantry 10. The input interface circuitry 43 may be configured as a tablet terminal or the like capable of wirelessly communicating with the body of the console 40.

The processing circuitry 44 controls the operation of the entire PCCT apparatus 1. The processing circuitry 44 has, for example, a system control function 441, a scan control function 442, a preprocessing function 443, a reconstruction function 444, a defect detection function 445, an acquisition function 446, a selection function 447, an interpolation target map generation function 448, a display control function 449, and a registration function 450. In the embodiment, each processing function performed by the system control function 441, the scan control function 442, the preprocessing function 443, the reconstruction function 444, the defect detection function 445, the acquisition function 446, the selection function 447, the interpolation target map generation function 448, the display control function 449, and the registration function 450 is stored in the memory 41 in the form of a computer program executable by a computer. The processing circuitry 44 is a processor that reads the computer programs from the memory 41 and executes the read computer programs, thereby implementing functions corresponding to the executed computer programs. In other words, the processing circuitry 44 in the state of having read the computer programs has the functions illustrated in the processing circuitry 44 in FIG. 1. The memory 41 is an example of a storage medium that is a non-transitory computer readable medium and includes instructions to be executed by a computer.

In FIG. 1, the system control function 441, the scan control function 442, the preprocessing function 443, the reconstruction function 444, the defect detection function 445, the acquisition function 446, the selection function 447, the interpolation target map generation function 448, the display control function 449, and the registration function 450 are described as being implemented by a single processor; however, the processing circuitry 44 may be configured by combining a plurality of independent processors and respective processors may implement functions by executing computer programs. In FIG. 1, single storage circuitry such as the memory 41 is described as storing a computer program corresponding to each processing function; however, a plurality of pieces of storage circuitry may be distributed and arranged, and the processing circuitry 44 may be configured to read a corresponding computer program from individual storage circuitry.

The term "processor" used in the above description, for example, means circuitry such as a central processing unit (CPU), a graphics processing unit (GPU), an application specific integrated circuit (ASIC), or a programmable logic device (for example, a simple programmable logic device (SPLD), a complex programmable logic device (CPLD), and a field programmable gate array (FPGA)). The processor implements functions by reading and executing the computer programs stored in the memory 41. Instead of storing the computer programs in the memory 41, the computer programs may be directly incorporated in the circuitry of the processor. In this case, the processor implements functions by reading and executing the computer programs incorporated in the circuitry.

When the X-ray detector 12 includes defective detection elements, CT image data may include noise such as artifacts. Therefore, the PCCT apparatus 1 performs a detection process of detecting defective detection elements at regular intervals such as daily. Subsequently, the processing circuitry 44 masks detection results of the defective detection elements. That is, the processing circuitry 44 does not use the detection results of the defective detection elements, and performs interpolation by using detection results of detection elements around the defective detection elements.

In order to reduce noise such as artifacts, the processing circuitry 44 needs to mask the detection results of the defective detection elements. However, when the detection results are permanently masked, the X-ray detector 12 has fewer unmasked detection elements. The detection process is also affected by various factors such as the temperature of a room where the PCCT apparatus 1 is installed. That is, whether detection elements are defective detection elements may vary.

Figure 2:
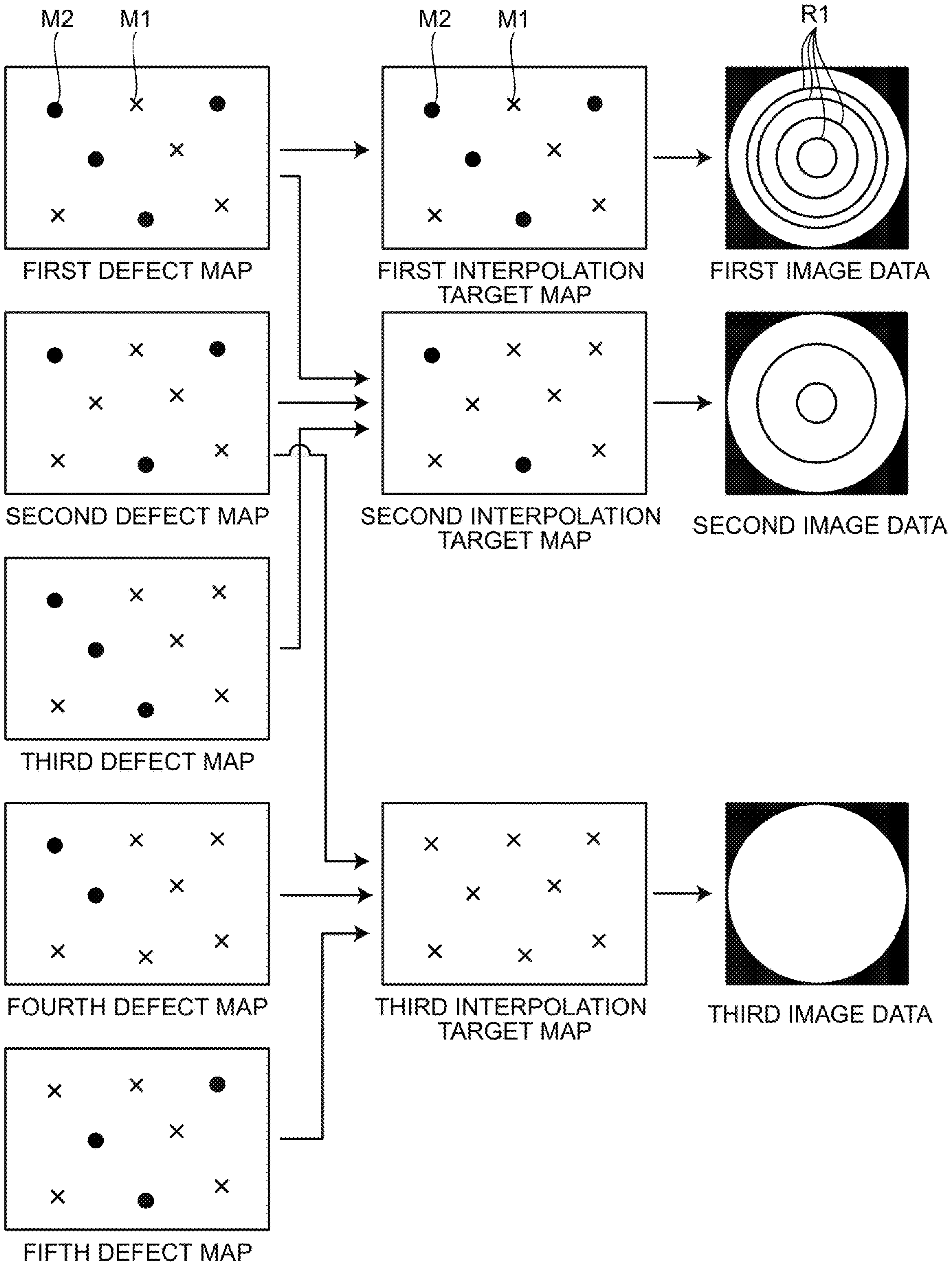
FIG. 2 is a diagram illustrating an example of an overview of a process of increasing the number of unmasked detection elements.

Therefore, the processing circuitry 44 increases the number of unmasked detection elements by the following process. FIG. 2 is a diagram illustrating an example of an overview of a process of increasing the number of unmasked detection elements. The acquisition function 446 acquires, from the memory 41, a defect map indicating the arrangement of defective detection elements in the X-ray detector 12. A first defect map, a second defect map, a third defect map, a fourth defect map, and a fifth defect map illustrated in FIG. 2 are defect maps at different timings.

In the defect maps illustrated in FIG. 2, a cross mark M1 indicates the arrangement of defective detection elements in the X-ray detector 12. In other words, the cross mark M1 indicates the arrangement of detection elements to be interpolated. A black mark M2 indicates the arrangement of detection elements not determined to be defective detection elements in the X-ray detector 12. In other words, the black mark M2 indicates the arrangement of detection elements having ever been detected as a defective detection element at any timing in defect maps acquired at different timings. That is, the black mark M2 indicates, among a plurality of defect maps acquired at at least a first timing and a second timing, the arrangement of detection elements detected as defective detection elements in the defect maps acquired at the first timing.

On the basis of a user's operation or the like, the selection function 447 selects a defect map serving as the basis of an interpolation target map from a plurality of defect maps acquired by the acquisition function 446. The interpolation target map is information indicating the arrangement of detection elements that are some of detection elements included in any of the plurality of defect maps acquired by the acquisition function 446 and whose detection results are not used. The detection elements whose detection results are not used are detection elements to be interpolated. That is, the detection results that are not used are interpolated using detection results of detection elements around the detection elements whose detection results are not used.

In the interpolation target map illustrated in FIG. 2, the cross mark M1 indicates the position where a defective detection element exists, like the defect map. In other words, the cross mark M1 indicates the arrangement of detection elements to be interpolated. That is, the detection result of the detection element corresponding to the cross mark M1 is not used to generate CT image data for use in image diagnosis for the subject P.

The black mark M2 indicates the arrangement of detection elements having ever been detected as defective detection elements like the defect map. In other words, the black mark M2 indicates the arrangement of detection elements whose detection results are not used. That is, the detection result of the detection element corresponding to the black mark M2 is used to generate CT image data for use in image diagnosis for the subject P.

On the basis of the defect map selected by the selection function 447, the interpolation target map generation function 448 generates an interpolation target map in which the detection result of the defective detection element indicated by the cross mark M1 is set as a mask target. That is, the interpolation target map generation function 448 generates an interpolation target map in which the detection result of the defective detection element indicated by the cross mark M1 is set to be interpolated by the detection results of surrounding detection elements, instead of being used to generate CT image data for use in image diagnosis for the subject P.

In FIG. 2, a first interpolation target map is generated on the basis of the first defect map. A second interpolation target map is generated on the basis of the first defect map, the second defect map, and the third defect map. A third interpolation target map is generated on the basis of the second defect map, the fourth defect map, and the fifth defect map.

On the basis of the detection data of the X-ray detector 12 and the interpolation target map, the preprocessing function 443 and the reconstruction function 444 generate interpolated data such as CT image data obtained by interpolating detection results. First image data is generated on the basis of the first interpolation target map and the detection data. The first image data includes four ring artifacts R1. Second image data is generated on the basis of the second interpolation target map and the detection data. The second image data includes two ring artifacts R1. Third image data is generated on the basis of the third interpolation target map and the detection data. The third image data includes no ring artifact R1. A user looks at each image data to determine which combination of the defect maps is optimal.

The registration function 450 registers an interpolation target map corresponding to a combination of defect maps determined by the user to be optimal, as a target for use in the examination of the subject P. In this way, the PCCT apparatus 1 allows the user to select a combination of defect maps. This allows the PCCT apparatus 1 to have more unmasked detection elements than when all defective detection elements shown in any of the defect maps are masked.

Each function is described in detail below.

The system control function 441 controls various functions of the processing circuitry 44 on the basis of input operations received from an operator via the input interface circuitry 43.

The scan control function 442 controls CT scan performed on the gantry 10. For example, the scan control function 442 controls the execution of various types of scan such as non-helical scan (conventional scan) and helical scan by controlling the operation of each part such as the X-ray detector 12, X-ray high voltage circuitry 14, the controller 15, the DAS 18, and table drive circuitry 32.

The preprocessing function 443 generates projection data by performing preprocessing such as logarithmic transformation, offset correction, inter-channel sensitivity correction, and beam hardening correction on the detection data output from the DAS 18.

The preprocessing function 443 performs preprocessing on the basis of the detection results by the X-ray detector 12 and the interpolation target map registered by the registration function 450. More specifically, the preprocessing function 443 performs preprocessing including, for example, interpolation with the detection results of detection elements around the defective detection elements without using the detection results of the defective detection elements shown in the interpolation target map. This allows the preprocessing function 443 to generate projection data interpolated by the detection results of the detection elements around the defective detection elements. That is, on the basis of the interpolation target map generated by the interpolation target map generation function 448, the preprocessing function 443 generates interpolated data by interpolating the detection results by the X-ray detector 12. The preprocessing function 443 may also perform interpolation by other methods as well as the interpolation method using the detection results of the detection elements around the defective detection elements.

The reconstruction function 444 generates CT image data by performing a reconstruction process using a filtered back projection method, a successive approximation reconstruction method, or the like on the projection data generated by the preprocessing function 443.

Interpolation to an interpolation target set in the interpolation target map may be performed by the reconstruction function 444 as well as the preprocessing function 443. For example, the reconstruction function 444 may interpolate CT image data in the reconstruction process. Alternatively, the preprocessing function 443 and the reconstruction function 444 may perform data interpolation in cooperation with each other. In this way, both or either of the preprocessing function 443 and the reconstruction function 444 is an example of an interpolation unit. Interpolated projection data or interpolated CT image data is an example of interpolated data.

The defect detection function 445 detects defective detection elements from the X-ray detector 12. The defective detection element is a detection element that outputs an abnormal detection result for incident X-rays. More specifically, the defect detection function 445 performs scan in order to calibrate each detection element of the X-ray detector 12. For example, the defect detection function 445 performs scan with no subject P inserted into the opening (bore) forming an imaging space and with air present. Thus, the defect detection function 445 acquires a plurality of projection data for each projection angle. The defect detection function 445 calculates an average value of pixels at the same location in the plurality of projection data. The defect detection function 445 compares the above average value with an average value of surrounding pixels, and determines that defective detection elements exist when the difference is equal to or greater than a threshold value. In this way, the defect detection function 445 detects defective detection elements. The method of detecting defective detection elements is merely an example, and the defect detection function 445 may detect defective detection elements by other methods.

The defect detection function 445 also generates a defect map indicating the arrangement of defective detection elements in the X-ray detector 12. Subsequently, the defect detection function 445 stores the generated defect map in the memory 41.

The acquisition function 446 acquires, from the memory 41 that stores defect maps indicating the arrangement of defective detection elements in the X-ray detector 12 including a plurality of detection elements that detect X-rays, a plurality of the defect maps at different timings. The acquisition function 446 is an example of an acquisition unit. That is, the acquisition function 446 acquires a plurality of defect maps of the X-ray detector 12 at different times. The acquisition function 446 may also acquire a defect map from a storage device connected via a network such as an in-hospital local area network (LAN), as well as the memory 41.

The selection function 447 selects one or more defect maps from the defect maps acquired by the acquisition function 446. For example, the selection function 447 selects a defect map on the basis of an operation received by the system control function 441.

Figure 3:
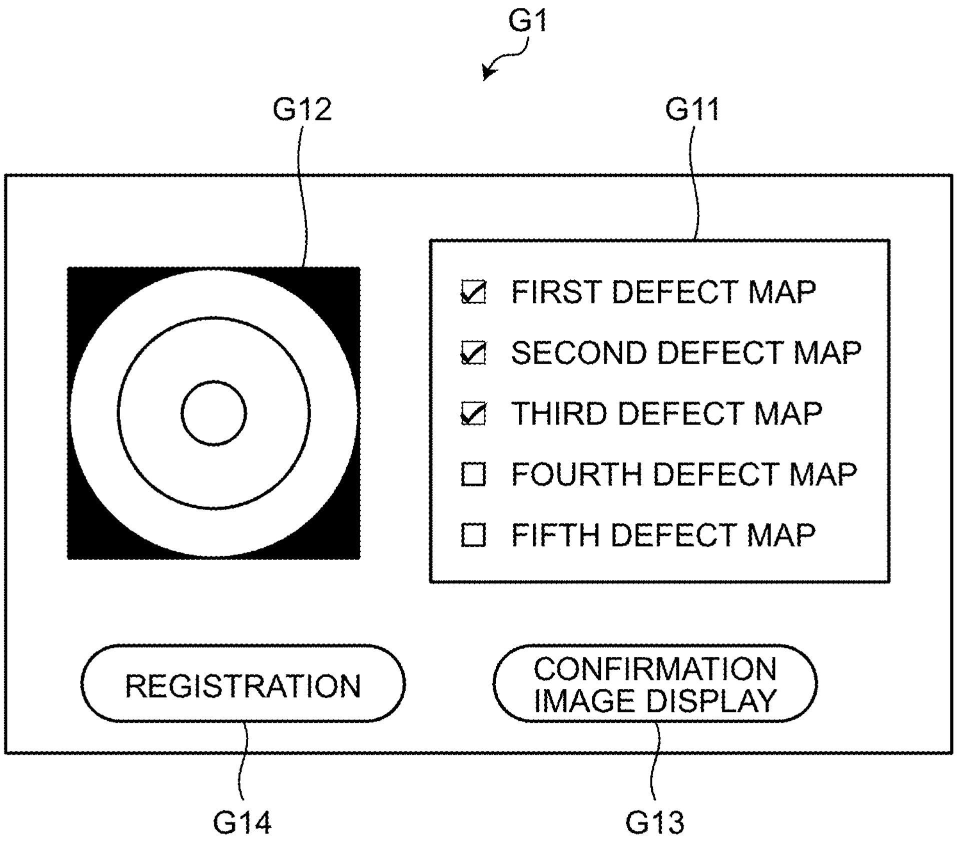
FIG. 3 is a diagram illustrating an example of a defect map selection image.

More specifically, the selection function 447 selects a defect map on the basis of the operation received by the system control function 441 in a selection image G11 of a defect map selection image G1 (see FIG. 3). That is, the selection function 447 receives an operation of selecting a defect map serving as the basis of an interpolation target map from the plurality of defect maps acquired by the acquisition function 446. The selection function 447 is an example of a selection unit.

The interpolation target map generation function 448 generates an interpolation target map regarding some detection elements included in any of the plurality of defect maps acquired by the acquisition function 446. The interpolation target map generation function 448 is an example of a generation unit. More specifically, the interpolation target map generation function 448 generates an interpolation target map on the basis of the defect maps selected by the selection function 447. That is, the interpolation target map generation function 448 generates an interpolation target map in which defective detection elements set in any of the defect maps selected by the selection function 447 are set as detection elements whose detection results are not used. In this way, the interpolation target map generation function 448 generates the interpolation target map by using the defect maps selected by the selection function 447, thereby increasing the number of detection elements whose detection results are available, compared to when all defect maps obtained by the acquisition function 446 are used.

The display control function 449 displays the defect map selection image G1 on the display 42. FIG. 3 is a diagram illustrates an example of the defect map selection image G1. The defect map selection image G1 is an image for selecting a defect map serving as the basis of an interpolation target map from the defect maps acquired by the acquisition function 446. The defect map selection image G1 includes the selection image G11, a confirmation image G12, a confirmation image display button G13, and a registration button G14. The display control function 449 is an example of a display control unit.

The selection image G11 is an image for receiving an operation of selecting a defect map serving as an interpolation target map. For example, the selection image G11 is a check box for each defect map. By designating the check box, a user designates a defect map corresponding to the check box.

The confirmation image G12 is interpolated data generated on the basis of the interpolation target map generated from the defect map selected in the selection image G11 and the detection data output from DAS18 as a scan result. For example, the confirmation image G12 is interpolated data such as CT image data generated by the reconstruction process of the reconstruction function 444 using the projection data interpolated by the preprocessing function 443.

The confirmation image display button G13 is a button for receiving an operation of displaying the confirmation image G12. More specifically, when the confirmation image display button G13 is pressed, the selection function 447 selects the defect map designated in the selection image G11. The interpolation target map generation function 448 generates an interpolation target map on the basis of the defect map selected by the selection function 447. The preprocessing function 443 performs preprocessing on the basis of the interpolation target map generated by the interpolation target map generation function 448 and the detection data scanned with the subject P not inserted in the bore. The reconstruction function 444 generates interpolated data such as CT image data on the basis of projection data generated by the preprocessing. Subsequently, the display control function 449 displays the generated interpolated data as the confirmation image G12.

The registration button G14 is a button for receiving an operation of registering an interpolation target map to be used for detection data obtained by scanning the subject P. In other words, the registration button G14 is a button for receiving an operation of registering an interpolation target map for clinical use.

The registration function 450 registers an interpolation target map for use in image diagnosis for the subject P. For example, the registration function 450 registers the use of the interpolation target map serving as the basis of the confirmation image G12 displayed by the display control function 449. The registration function 450 is an example of a registration unit. For example, when the registration button G14 is pressed, the registration function 450 registers the interpolation target map.

The process performed by the PCCT apparatus 1 is described below.

Figure 4:
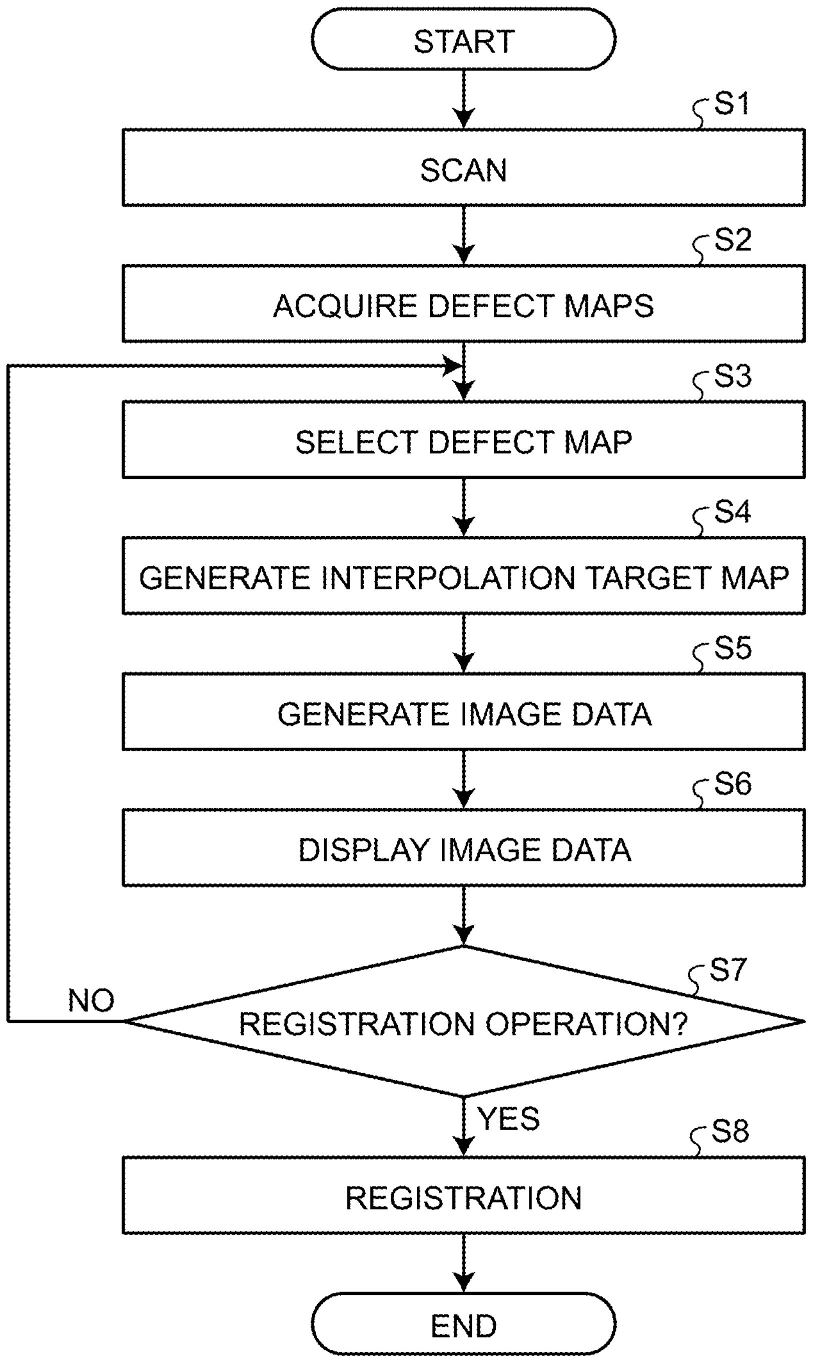
FIG. 4 is a flowchart illustrating an example of a registration process performed by the PCCT apparatus according to the first embodiment.

FIG. 4 is a flowchart illustrating an example of the registration process performed by the PCCT apparatus 1 according to the first embodiment.

The scan control function 442 scans the subject P in a state where the subject P is not inserted in the bore of the gantry 10 (step S1).

The acquisition function 446 acquires a plurality of defect maps stored in the memory 41 (step S2).

The selection function 447 selects a defect map corresponding to an operation received in the selection image G11 (step S3).

The interpolation target map generation function 448 generates an interpolation target map in which the detection results of defective detection elements indicated in the defect map selected by the selection function 447 are set as interpolation targets (step S4).

The preprocessing function 443 and the reconstruction function 444 generate interpolated data such as CT image data on the basis of detection data generated by the scan at step S1 and the interpolation target map (step S5).

The display control function 449 displays the generated interpolated data as the confirmation image G12 (step S6).

The system control function 441 determines whether an operation of registering a map as an interpolation target map to be used with the subject P inserted in the bore is received (step S7). When the operation of registering is not received (No at step S7), the selection function 447 selects a defect map at step S3.

When the operation of registering is received (Yes at step S7), the registration function 450 registers the map as the interpolation target map to be used with the subject P inserted in the bore (step S8).

With the above, the PCCT apparatus 1 ends the registration process.

As described above, the PCCT apparatus 1 according to the first embodiment acquires a defect map stored in the memory 41 or the like. The PCCT apparatus 1 also generates an interpolation target map in which some of detection elements included in the acquired defect map are set. For example, the PCCT apparatus 1 generates an interpolation target map on the basis of a selected defect map in the defect map selection image G1. Subsequently, on the basis of the interpolation target map and the detection results by the X-ray detector 12, the PCCT apparatus 1 generates interpolated data such as CT image data obtained by interpolating detection results to be interpolated. In this way, the PCCT apparatus 1 generates an interpolation target map in which not all defective detection elements included in the acquired defect map but some of the defective detection elements are set as interpolation targets, thereby increasing the number of detection elements whose detection results are available compared to when the detection results of all the defective detection elements included in the defect map are interpolated.

First Modification

Figure 5:
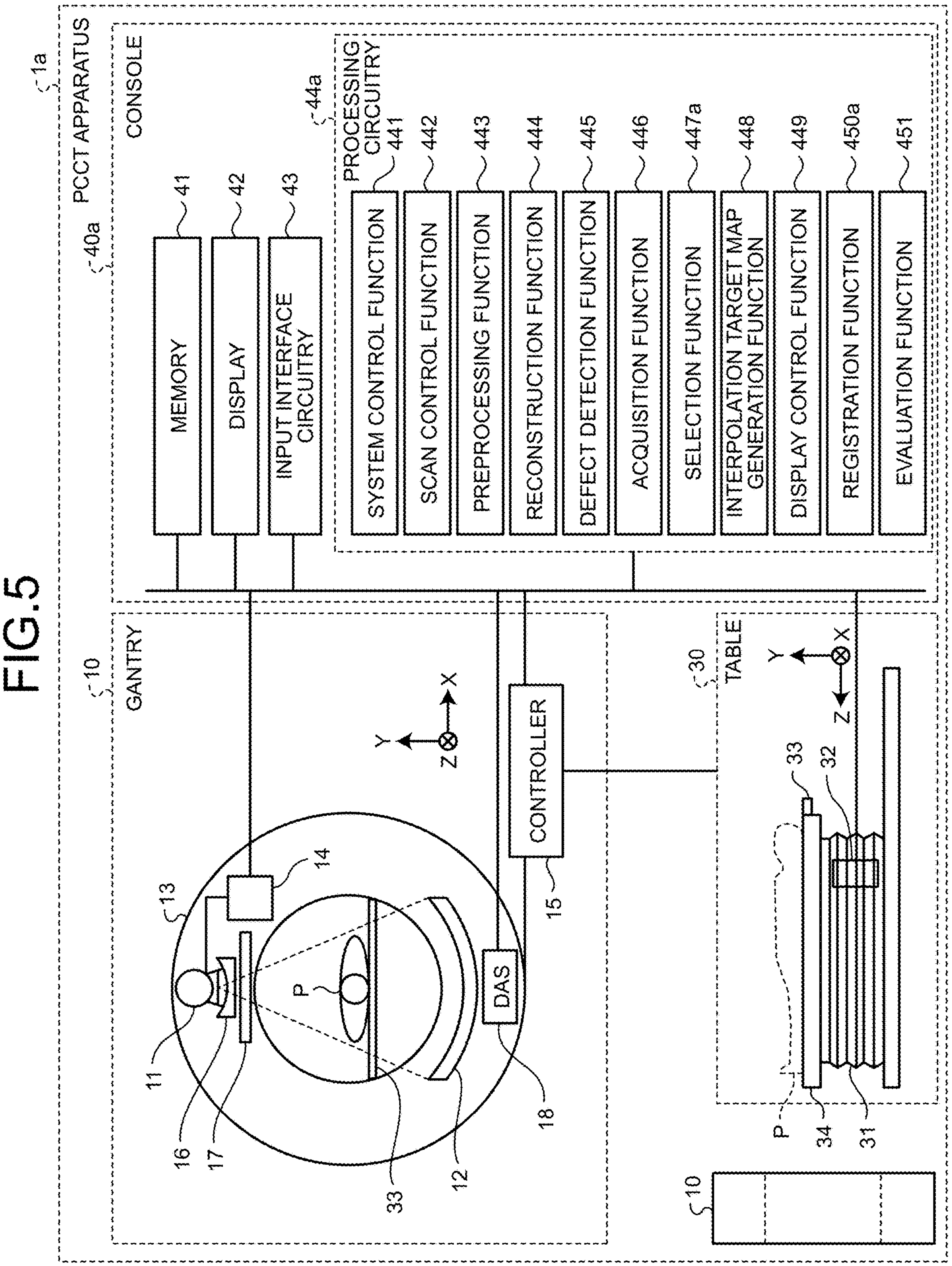
FIG. 5 is a diagram illustrating an example of the configuration of a PCCT apparatus according to a first modification.

FIG. 5 is a diagram illustrating an example of the configuration of a PCCT apparatus 1*a* according to a first modification. In the PCCT apparatus 1 according to the first embodiment, a user selects a combination of defect maps serving as the basis of an interpolation target map. In the PCCT apparatus 1 according to the first embodiment, a user determines the effect of an interpolation target map by looking at interpolated data to which the interpolation target map had been applied.

On the other hand, the PCCT apparatus 1*a* according to the first modification automates these processes. That is, the PCCT apparatus 1*a* generates an interpolation target map with all combinations of defect maps. The PCCT apparatus 1*a* also evaluates interpolated data to which the interpolation target map has been applied, on the basis of an evaluation criterion. Subsequently, the PCCT apparatus 1*a* registers the interpolation target map on the basis of evaluation results.

Processing circuitry 44*a* of a console 40*a* has an evaluation function 451.

A selection function 447*a* selects a combination of one or more defect maps from the plurality of defect maps acquired by the acquisition function 446. The selection function 447*a* repeats the above process until all combinations are selected.

The interpolation target map generation function 448 generates an interpolation target map in which the detection results of defective detection elements set in any of the defect maps selected by the selection function 447*a* are set as detection elements that are not used. That is, the interpolation target map generation function 448 generates an interpolation target map for each combination of the plurality of defect maps acquired by the acquisition function 446.

At least one of the preprocessing function 443 and the reconstruction function 444 generates, on the basis of the interpolation target map generated by the interpolation target map generation function 448 and the detection results by the X-ray detector 12, interpolated data, such as CT image data in which the detection results of the defective detection elements are interpolated, for each combination of the defect maps selected by the selection function 447*a*.

The evaluation function 451 evaluates the interpolated data such as CT image data generated by the preprocessing function 443 and the reconstruction function 444. The evaluation function 451 is an example of an evaluation unit. That is, the evaluation function 451 evaluates the interpolated data generated for each combination of the defect maps.

More specifically, the evaluation function 451 evaluates the interpolated data such as CT image data to which the interpolation target map has been applied, on the basis of the evaluation criterion, thereby evaluating each of a plurality of interpolation target maps. For example, the evaluation criterion is a standard deviation (SD) value representing noise in the interpolated data, or the like. That is, on the basis of noise in the interpolated data to which the interpolation target map has been applied, the evaluation function 451 evaluates each of the plurality of interpolation target maps.

On the basis of the evaluation results by the evaluation function 451, a registration function 450*a* registers that the interpolation target map serving as the basis of the interpolated data evaluated by the evaluation function 451 is used for image diagnosis for the subject P. More specifically, on the basis of the evaluation results by the evaluation function 451, the registration function 450*a* selects the interpolation target map. Subsequently, the registration function 450*a* registers the selected interpolation target map.

The process performed by the PCCT apparatus 1*a* is described below.

Figure 6:
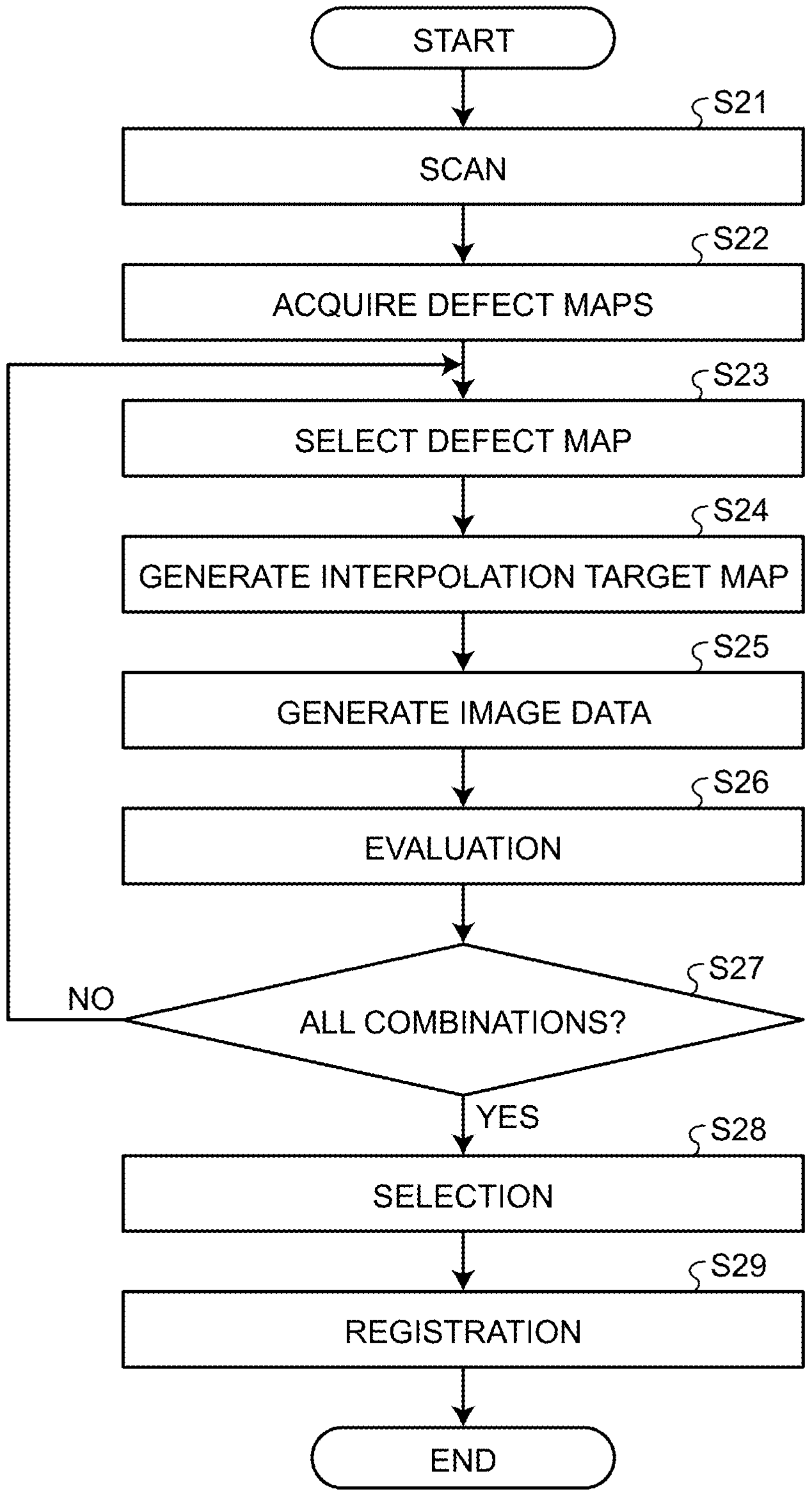
FIG. 6 is a flowchart illustrating an example of a registration process performed by the PCCT apparatus according to the first modification.

FIG. 6 is a flowchart illustrating an example of a registration process performed by the PCCT apparatus 1*a* according to the first modification.

The scan control function 442 scans the subject P in a state where the subject P is not inserted in the bore of the gantry 10 (step S21).

The acquisition function 446 acquires a plurality of defect maps stored in the memory 41 (step S22).

The selection function 447*a* selects a defect map corresponding to an operation received in the selection image G11 (step S23).

The interpolation target map generation function 448 generates an interpolation target map in which the detection results of defective detection elements indicated in the defect map selected by the selection function 447*a* are set as interpolation targets (step S24).

The preprocessing function 443 and the reconstruction function 444 generate interpolated data such as CT image data on the basis of detection data generated by the scan at step S21 and the interpolation target map (step S25).

The evaluation function 451 evaluates the interpolation target map on the basis of the interpolated data to which the interpolation target map generated by the interpolation target map generation function 448 has been applied (step S26).

The evaluation function 451 determines whether interpolation target maps generated by all combinations of the defect maps have been evaluated (step S27).

When the evaluation for all the interpolation target maps has not ended (No at step S27), the selection function 447*a* proceeds to step S23 to select a combination of defect maps that have not yet been selected.

When the evaluation for all the interpolation target maps has ended (Yes at step S27), the registration function 450*a* selects interpolation target maps on the basis of the evaluation results by the evaluation function 451 (step S28). The registration function 450*a* registers the selected interpolation target maps as interpolation target maps for use in image diagnosis for the subject P (step S29).

With the above, the PCCT apparatus 1*a* ends the registration process.

As described above, the PCCT apparatus 1*a* according to the first modification evaluates interpolated data, to which an interpolation target map has been applied, for each combination of defect maps serving as the basis of the interpolation target map. Subsequently, the PCCT apparatus 1*a* registers the interpolation target map selected on the basis of evaluation results as an interpolation target map for use in image diagnosis for the subject P. In this way, even though no operation is received from a user, the PCCT apparatus 1*a* can increase the number of detection elements whose detection results are available.

Second Embodiment

Figure 7:
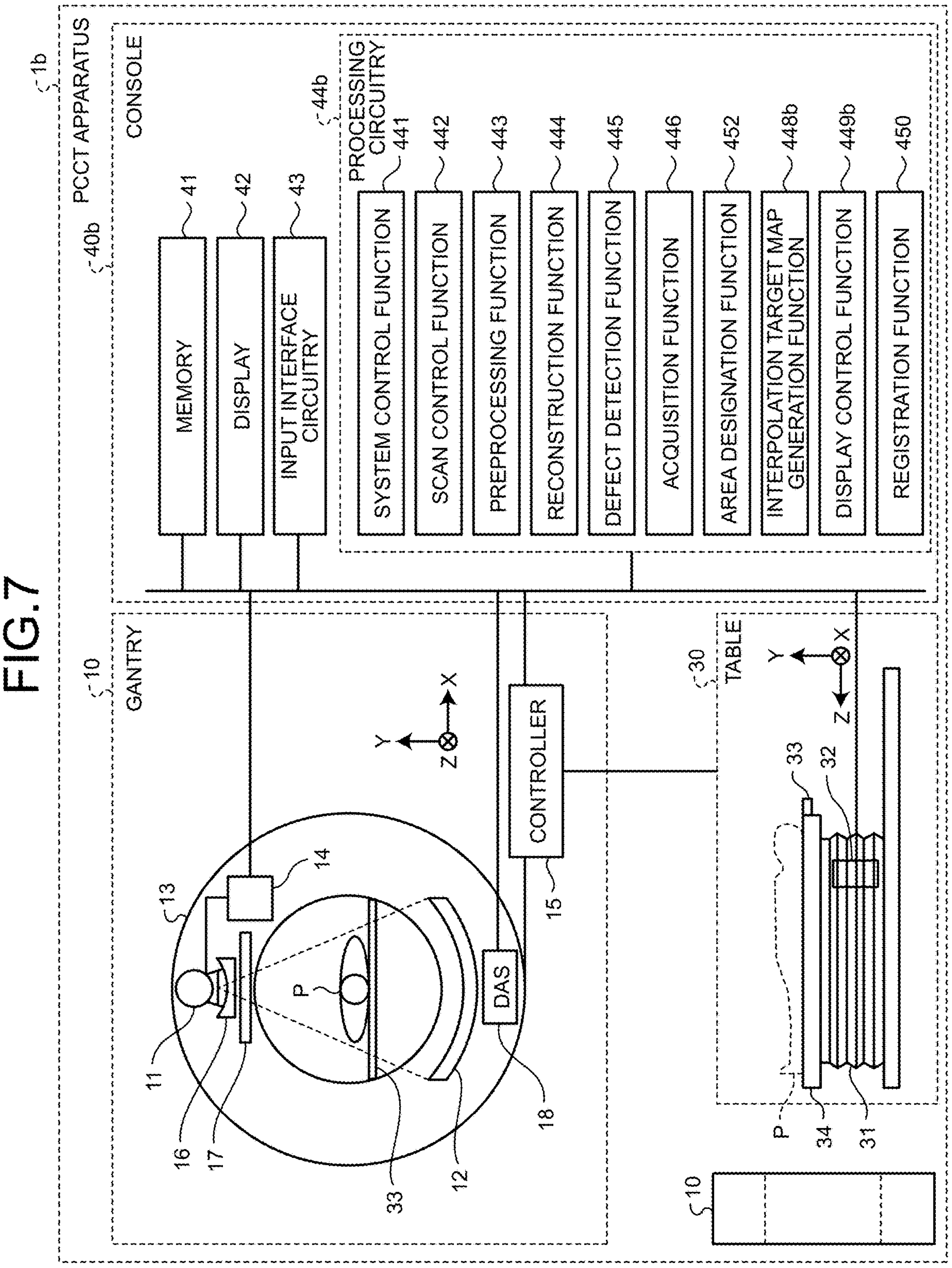
FIG. 7 is a diagram illustrating an example of a PCCT apparatus according to a second embodiment.

FIG. 7 is a diagram illustrating an example of a PCCT apparatus 1*b* according to a second embodiment. Processing circuitry 44*b* of a console 40*b* has an area designation function 452.

Figure 8:
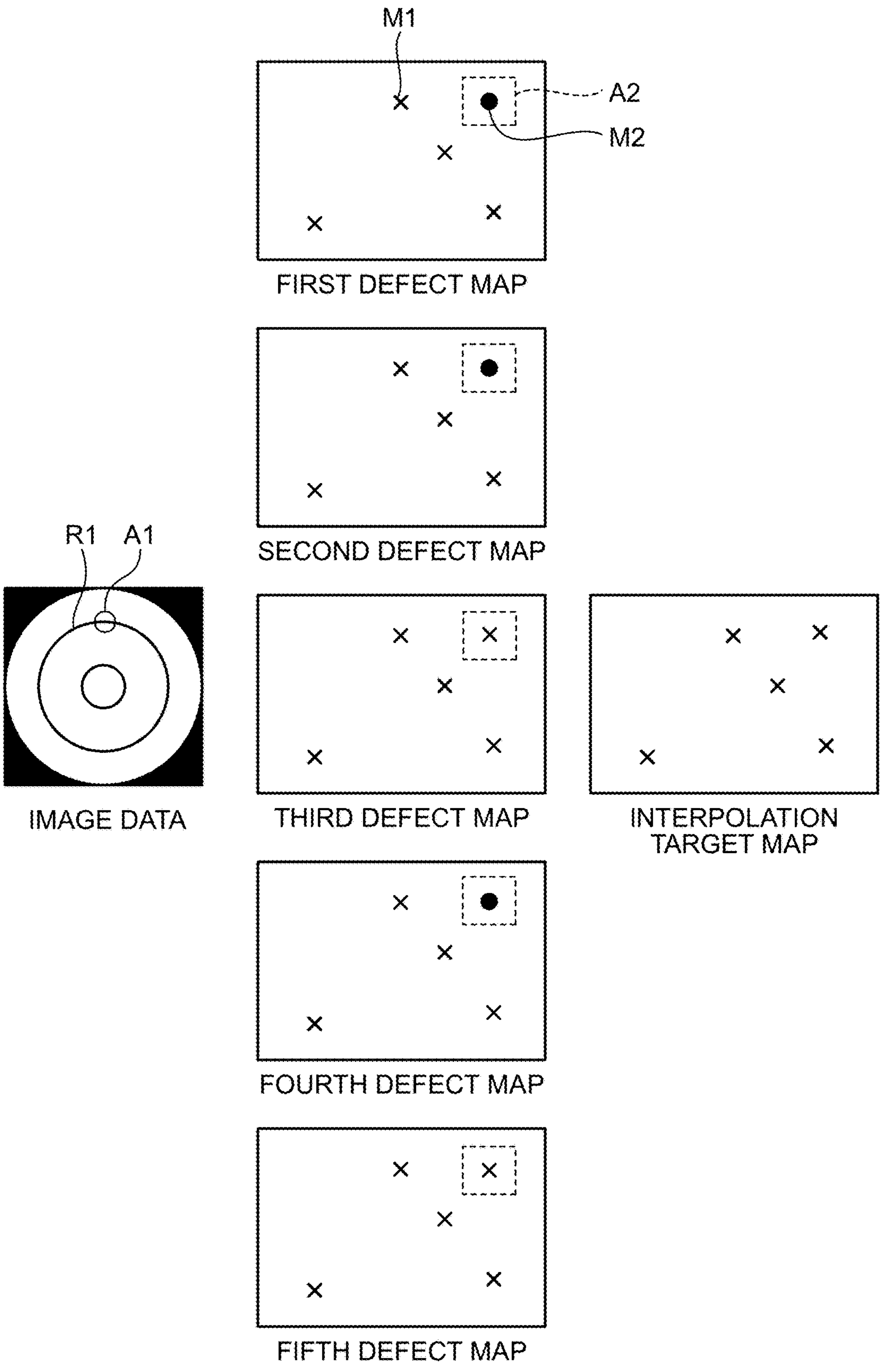
FIG. 8 is a diagram illustrating an example of an overview of a process performed by the PCCT apparatus according to the second embodiment.

FIG. 8 is a diagram illustrating an example of an overview of a process performed by the PCCT apparatus 1*b* according to the second embodiment. A display control function 449*b* displays CT image data based on the detection results by the X-ray detector 12. When a defective detection element exists in the X-ray detector 12, the CT image data includes noise such as the ring artifact R1.

The area designation function 452 receives an operation of designating a noise area A1 including noise such as the ring artifact R1 in the CT image data displayed by the display control function 449*b*. The area designation function 452 is an example of a designation unit. The noise area A1 is an example of a first area. More specifically, the area designation function 452 designates the noise area A1 on the basis of the operation received by the system control function 441.

An interpolation target map generation function 448*b* generates an interpolation target map on the basis of the plurality of defect maps acquired by the acquisition function 446 and the noise area A1.

More specifically, the interpolation target map generation function 448*b* specifies, for each of the plurality of defect maps acquired by the acquisition function 446, a search area A2 being an area on a defect map corresponding to the noise area A1. The interpolation target map generation function 448*b* is an example of a specifying unit. The search area A2 is an example of a second area. Specifically, the interpolation target map generation function 448*b* specifies the search area A2 on a defect map where a detection element that outputs a detection result serving as the basis of each pixel in the noise area A1 is arranged, by a process such as forward projection.

The interpolation target map generation function 448*b* generates an interpolation target map indicating the arrangement of detection elements that are defective detection elements included in the search area A2 of any of the plurality of defect maps acquired by the acquisition function 446 and interpolate detection results. The interpolation target map generation function 448*b* searches for defective detection elements included in the search area A2 of each defect map. Subsequently, the interpolation target map generation function 448*b* generates an interpolation target map in which detection results of the defective detection elements included in the search area A2 are set as interpolation targets.

The preprocessing function 443 and the reconstruction function 444 generate interpolated data such as CT image data on the basis of the interpolation target map generated by the interpolation target map generation function 448*b* and the detection results by the X-ray detector 12. More specifically, the preprocessing function 443 performs preprocessing on the basis of the interpolation target map generated by the interpolation target map generation function 448*b* and detection data scanned with the subject P not inserted in the bore. The reconstruction function 444 generates interpolated data such as CT image data on the basis of projection data generated by the preprocessing.

The display control function 449*b* displays the interpolated data to which the interpolation target map generated by the interpolation target map generation function 448*b* has been applied. That is, the display control function 449*b* requests a user to confirm whether an appropriate interpolation target map has been generated.

The registration function 450 registers the interpolation target map generated by the interpolation target map generation function 448*b* as an interpolation target map to be used for the detection data obtained by scanning the subject P. For example, when the system control function 441 receives an operation of registering an interpolation target map, the registration function 450 registers the interpolation target map.

The process performed by the PCCT apparatus 1*b* is described below.

Figure 9:
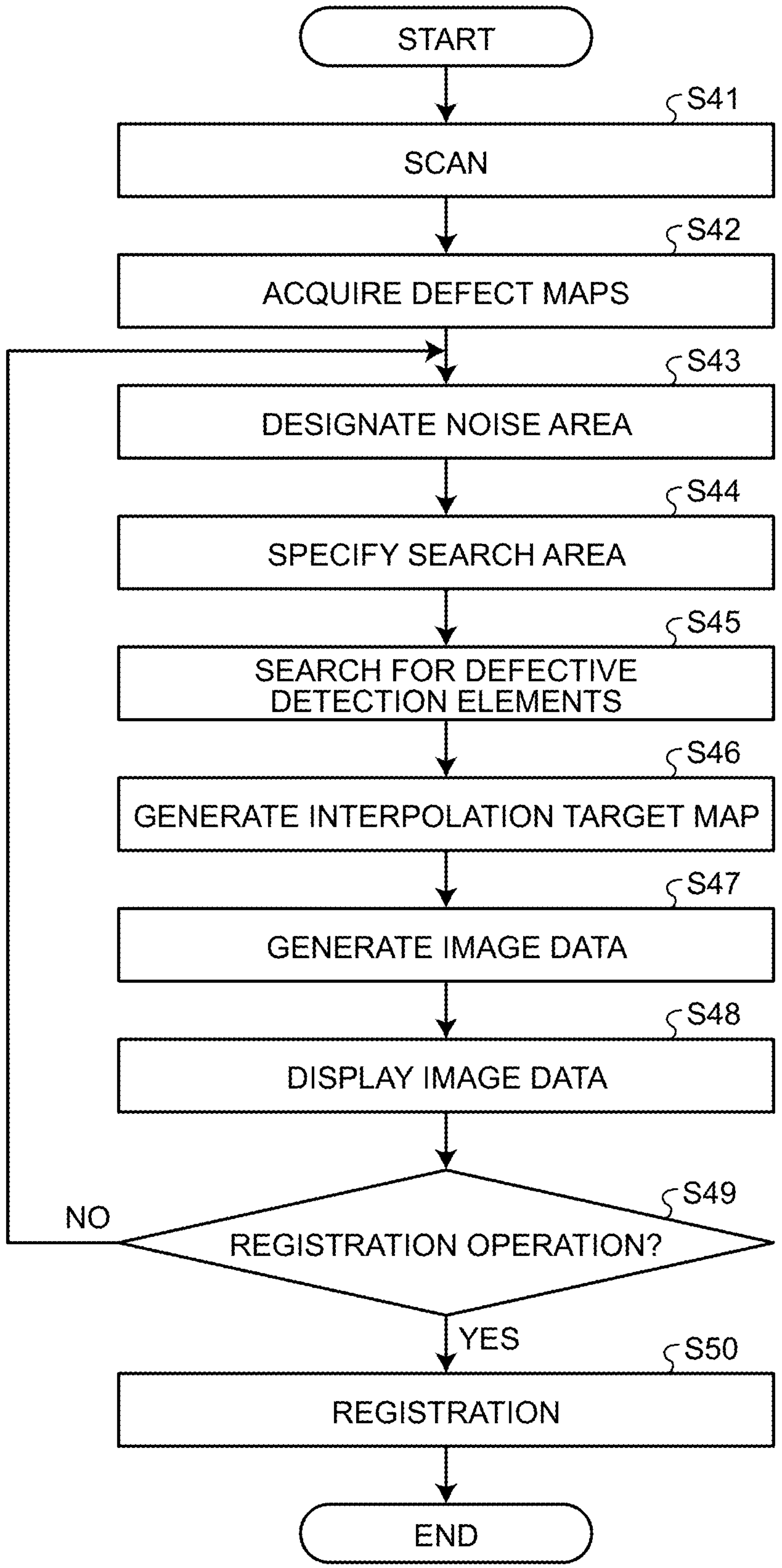
FIG. 9 is a flowchart illustrating an example of a registration process performed by the PCCT apparatus according to the second embodiment.

FIG. 9 is a flowchart illustrating an example of the registration process performed by the PCCT apparatus 1*b* according to the second embodiment.

The scan control function 442 scans the subject P in a state where the subject P is not inserted in the bore of the gantry 10 (step S41).

The acquisition function 446 acquires a plurality of defect maps stored in the memory 41 (step S42).

The area designation function 452 designates the noise area A1 on the basis of an operation received by the system control function 441 (step S43).

The interpolation target map generation function 448*b* specifies the search area A2 corresponding to the noise area A1 (step S44).

The interpolation target map generation function 448*b* searches for defective detection elements included in the search area A2 of each defect map acquired by the acquisition function 446 (step S45).

The interpolation target map generation function 448*b* generates an interpolation target map in which detection results of the defective detection elements included in the search area A2 are set as interpolation targets (step S46).

The preprocessing function 443 and the reconstruction function 444 generate interpolated data such as CT image data on the basis of detection data generated by the scan at step S41 and the interpolation target map (step S47).

The display control function 449*b* displays the generated interpolated data (step S48).

The system control function 441 determines whether an operation of registering the interpolation target map is received (step S49). When the operation of registering the interpolation target map is not received (No at step S49), the area designation function 452 proceeds to step S43 to designate the noise area A1 again.

When the operation of registering the interpolation target map is received (Yes at step S49), the registration function 450 registers the interpolation target map as an interpolation target map to be used with the subject P inserted in the bore (step S50).

With the above, the PCCT apparatus 1*b* ends the registration process.

As described above, the PCCT apparatus 1*b* according to the second embodiment receives an operation of designating the noise area A1 including noise such as the ring artifact R1 in an image in which CT image data is displayed. The PCCT apparatus 1*b* specifies the search area A2 on a defect map where a detection element that outputs a detection result serving as the basis of a pixel included in the noise area A1 is arranged. Subsequently the PCCT apparatus 1*b* generates an interpolation target map in which detection results of defective detection elements included in the search area A2 are set as interpolation targets. In this way, the PCCT apparatus 1*b* generates an interpolation target map on the basis of the noise area A1 including noise such as the ring artifact R1. Consequently, the PCCT apparatus 1*b* does not interpolate detection results of detection elements more than necessary, thereby increasing the number of detection elements whose detection results are available.

Third Embodiment

Figure 10:
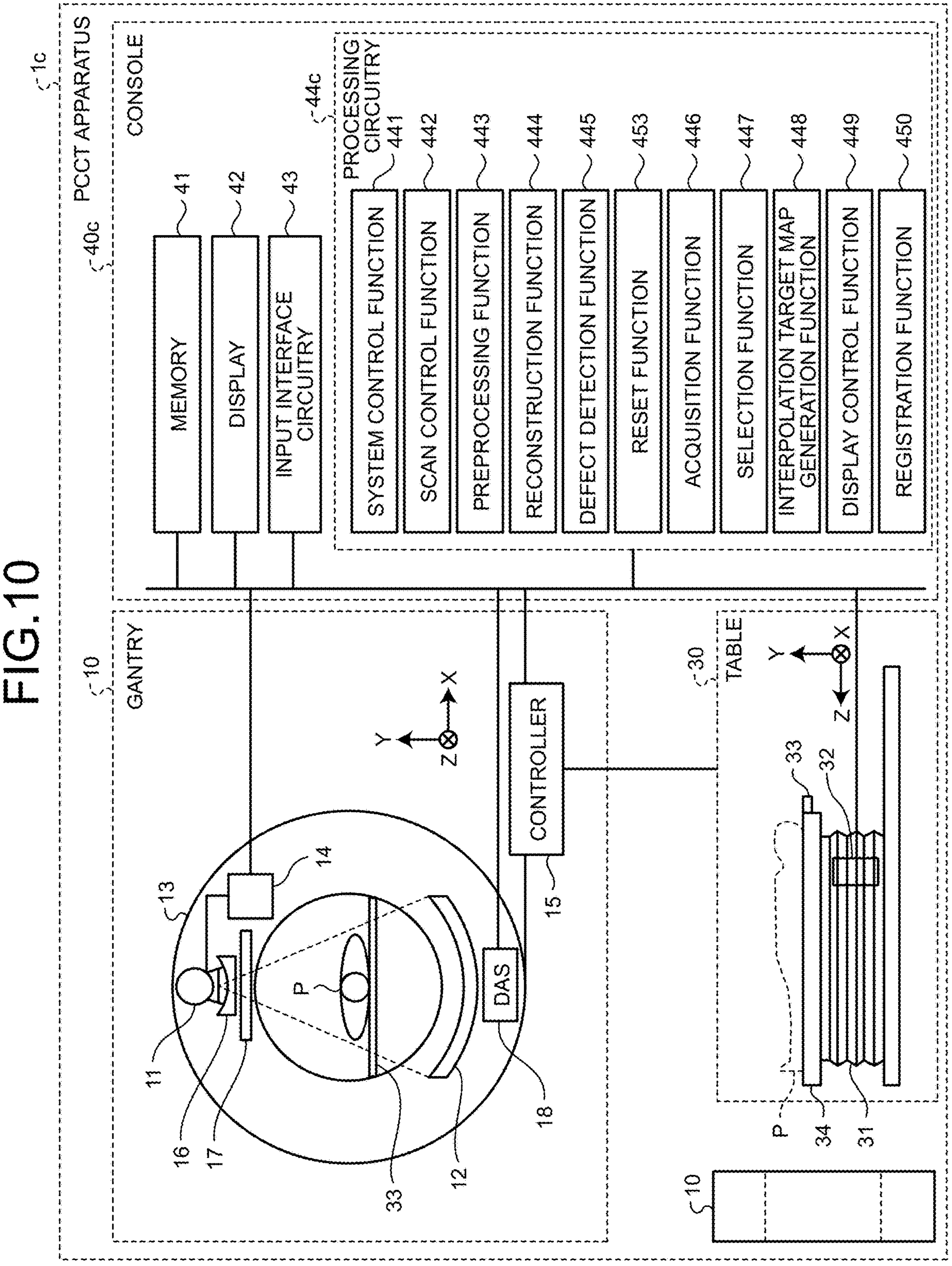
FIG. 10 is a diagram illustrating an example of a PCCT apparatus according to a third embodiment.

FIG. 10 is a diagram illustrating an example of a PCCT apparatus 1*c* according to a third embodiment. Processing circuitry 44*c* of a console 40*c* has a reset function 453 that resets the defect map stored in the memory 41.

The reset function 453 resets a defect map when a reset condition is satisfied. The reset function 453 is an example of a reset unit. For example, when routine maintenance of the PCCT apparatus 1*c* is performed, the reset function 453 resets the defect map acquired by the acquisition function 446. When the total number of defective detection elements shown in the defect map stored in the memory 41 is equal to or greater than a threshold value, the reset function 453 may reset an acquisition target.

When the number of defect maps stored in the memory 41 is equal to or greater than a set number, the reset function 453 may reset the acquisition target. The set number may be set by a user.

The acquisition function 446 acquires a defect map generated after the reset. That is, the acquisition function 446 acquires the defect map stored in the memory 41 after the reset.

The reset function 453 may also reset some of the defect maps. For example, when a variation in the detection results of defective detection element in the defect map is equal to or less than a threshold value, the reset function 453 resets the defect map of the defective detection element. In other words, the reset function 453 cancels the configuration with the defective detection element.

As described above, the PCCT apparatus 1*c* according to the third embodiment resets a defect map when the reset condition is satisfied. Subsequently, the PCCT apparatus 1*c* generates an interpolation target map by using a defect map after the reset. Consequently, the PCCT apparatus 1*c* can increase the number of detection elements whose detection results are available.

According to at least one embodiment described above, the number of detection elements whose detection results are available can be increased.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to:

acquire, from a storage unit that stores defect maps indicating an arrangement of defective detection elements in an X-ray detector comprising a plurality of detection elements that detect X-rays, a plurality of the defect maps at different timings;

generate an interpolation target map in which a detection result of a detection element determined as defective in each of the plurality of the acquired defect maps is set as an interpolation target, and a detection result of a detection element is set available when the detection element is determined as defective in any one of the plurality of the acquired defect maps and determined as non-defective in another defect map; and generate interpolated data, in which detection results by the X-ray detector are interpolated, on the basis of the generated interpolation target map.

2. The medical image processing apparatus according to claim 1, wherein the processing circuitry receives an operation of selecting the defect map serving as a basis of the interpolation target map from the plurality of the acquired defect maps, and generates the interpolation target map on the basis of the defect map selected by the received operation.

3. The medical image processing apparatus according to claim 1, wherein the processing circuitry displays the interpolated data.

4. The medical image processing apparatus according to claim 3, wherein the processing circuitry displays the interpolated data and an image for receiving an operation of selecting the defect map serving as a basis of the interpolation target map.

5. The medical image processing apparatus according to claim 3, wherein the processing circuitry registers use of the interpolation target map serving as a basis of the displayed interpolated data.

6. The medical image processing apparatus according to claim 1, wherein the processing circuitry displays image data based on the detection results by the X-ray detector, receives an operation of designating a first area where noise included in the displayed image data exists, and generates the interpolation target map on the basis of the plurality of the acquired defect maps and the first area.

7. The medical image processing apparatus according to claim 6, wherein the processing circuitry specifies a second area on the defect map corresponding to the first area, and generates the interpolation target map indicating an arrangement of the detection elements that are defective detection elements included in the second area in any of the plurality of the acquired defect maps and interpolate detection results.

8. The medical image processing apparatus according to claim 1, wherein the processing circuitry evaluates the generated interpolated data, and registers use of the interpolation target map serving as a basis of the evaluated interpolated data on the basis of a result of the evaluation.

9. The medical image processing apparatus according to claim 8, wherein the processing circuitry generates the interpolation target map for each combination of the plurality of the acquired defect maps, generates, on the basis of the interpolation target map and the detection results by the X-ray detector, the interpolated data in which the detection results of the defective detection elements are interpolated, for each combination of the defect maps, evaluates the generated interpolated data for each combination of the defect maps, and registers use of the interpolation target map serving as a basis of the interpolated data on the basis of a result of the evaluation.

10. The medical image processing apparatus according to claim 1, wherein the processing circuitry resets a defect map when a reset condition is satisfied, and acquires the defect map generated after the reset.

11. A medical image processing method comprising:

acquiring, from a storage unit that stores defect maps indicating an arrangement of defective detection elements in an X-ray detector having a plurality of detection elements that detect X-rays, a plurality of the defect maps at different timings;

generating an interpolation target map in which a detection result of a detection element determined as defective in each of the plurality of the acquired defect maps is set as an interpolation target, and a detection result of a detection element is set available when the detection element is determined as defective in any one of the plurality of the acquired defect maps and determined as non-defective in another defect map; and generating, on the basis of the interpolation target map and detection results by the X-ray detector, interpolated data in which the detection results are interpolated.

12. A non-transitory computer readable medium comprising instructions that cause a computer to execute:

acquiring, from a storage unit that stores defect maps indicating an arrangement of defective detection elements in an X-ray detector having a plurality of detection elements that detect X-rays, a plurality of the defect maps at different timings;

generating an interpolation target map in which a detection result of a detection element determined as defective in each of the plurality of the acquired defect maps is set as an interpolation target, and a detection result of a detection element is set available when the detection element is determined as defective in any one of the plurality of the acquired defect maps and determined as non-defective in another defect map; and generating, on the basis of the interpolation target map and detection results by the X-ray detector, interpolated data in which the detection results are interpolated.

* * * * *